(12) United States Patent
Lando et al.

(10) Patent No.: US 10,709,897 B2
(45) Date of Patent: Jul. 14, 2020

(54) TREATMENT INTERVALS FOR USE OF COMPOSITIONS COMPRISING ENERGY ABSORBING MATERIALS FOR DERMATOLOGICAL APPLICATIONS

(71) Applicant: Sebacia, Inc., Duluth, GA (US)

(72) Inventors: Anthony V. Lando, Suwanee, GA (US); Dilip Paithankar, Wayland, MA (US); Erin C. Keller, Atlanta, GA (US); Todd J. Meyer, Roswell, GA (US)

(73) Assignee: Sebacia, Inc., Duluth, GA (US)

( * ) Notice: Subject to any disclaimer, the term of this patent is extended or adjusted under 35 U.S.C. 154(b) by 627 days.

(21) Appl. No.: 14/593,199

(22) Filed: Jan. 9, 2015

(65) Prior Publication Data

US 2015/0196639 A1    Jul. 16, 2015

Related U.S. Application Data

(60) Provisional application No. 61/926,063, filed on Jan. 10, 2014.

(51) Int. Cl.
*A61N 5/02* (2006.01)
*A61N 5/06* (2006.01)
(Continued)

(52) U.S. Cl.
CPC .......... *A61N 5/0616* (2013.01); *A61B 18/203* (2013.01); *A61K 8/0241* (2013.01); *A61K 8/19* (2013.01); *A61K 8/86* (2013.01); *A61K 9/0009* (2013.01); *A61K 9/0014* (2013.01); *A61K 9/10* (2013.01); *A61K 9/5115* (2013.01);
(Continued)

(58) Field of Classification Search
CPC ........ A61N 5/0616; A61N 5/062; A61N 7/00; A61B 18/203; A61B 2018/00452; A61B 2018/00458; A61B 2018/0047; A61B 2018/00476; A61K 9/0014; A61K 8/0241; A61K 8/19; A61K 8/86; A61K 9/0009; A61K 9/10; A61K 9/5115; A61K 41/0061; A61K 47/10; A61K 49/0047; A61K 2800/412; A61K 2800/624; A61K 2800/656; A61K 2800/81; A61K 2800/82;
(Continued)

(56) References Cited

U.S. PATENT DOCUMENTS

2008/0188558 A1\* 8/2008 Godal .................. A61K 31/197
514/529
2009/0302029 A1\* 12/2009 Krishna .................. A61N 5/00
219/678
(Continued)

*Primary Examiner* — Kami A Bosworth
(74) *Attorney, Agent, or Firm* — Edwin S. Flores; Daniel J. Chalker; Chalker Flores, LLP

(57) ABSTRACT

The present invention provides compositions comprising energy (e.g., light) absorbing submicron particles (e.g., nanoparticles comprising a silica core and a gold shell) and methods for delivering such particles via topical application. This delivery is facilitated by application of mechanical agitation (e.g. massage), acoustic vibration in the range of 10 Hz-20 kHz, ultrasound, alternating suction and pressure, and microjets. The method of treatment is performed and then, depending upon the desired clinical outcome, repeated after a treatment response interval has elapsed.

40 Claims, 6 Drawing Sheets

(51) Int. Cl.
   *A61K 41/00*    (2020.01)
   *A61K 9/00*     (2006.01)
   *A61B 18/20*    (2006.01)
   *A61K 49/00*    (2006.01)
   *A61K 9/51*     (2006.01)
   *A61K 8/19*     (2006.01)
   *A61K 9/10*     (2006.01)
   *A61Q 19/00*    (2006.01)
   *A61K 8/86*     (2006.01)
   *A61K 47/10*    (2017.01)
   *A61N 7/00*     (2006.01)
   *A61K 8/02*     (2006.01)
   *A61Q 9/04*     (2006.01)
   *A61B 18/00*    (2006.01)

(52) U.S. Cl.
   CPC .......... *A61K 41/0061* (2013.01); *A61K 47/10* (2013.01); *A61K 49/0047* (2013.01); *A61N 5/062* (2013.01); *A61N 7/00* (2013.01); *A61Q 9/04* (2013.01); *A61Q 19/008* (2013.01); *A61B 2018/00476* (2013.01); *A61K 2800/412* (2013.01); *A61K 2800/624* (2013.01); *A61K 2800/651* (2013.01); *A61K 2800/81* (2013.01); *A61K 2800/82* (2013.01)

(58) Field of Classification Search
   CPC ....... A61Q 19/00; A61Q 19/008; A61P 17/00; A61P 17/02; A61P 17/08; A61P 43/00
   See application file for complete search history.

(56) References Cited

U.S. PATENT DOCUMENTS

| | | | |
|---|---|---|---|
| 2010/0298444 A1* | 11/2010 | Diaz Alperi | A61K 36/9066 514/679 |
| 2012/0059307 A1* | 3/2012 | Harris | A61K 8/0245 604/20 |
| 2013/0315999 A1 | 11/2013 | Paithankar et al. | |
| 2014/0079686 A1* | 3/2014 | Barman | A61K 8/69 424/94.67 |

* cited by examiner

| | Treatment | Control |
|---|---|---|
| WEIGHTED INFLAMMATORY LESION COUNTS 12 weeks POST 2ND OF 2 TREATMENTS | | |
| N | 14 | 14 |
| Mean % change from BL | -47% | +1% |

NOT STATISTICALLY SIGNIFICANT

TREATMENT INTERVALS FOR USE OF COMPOSITIONS COMPRISING ENERGY ABSORBING MATERIALS FOR DERMATOLOGICAL APPLICATIONS

CROSS REFERENCE TO RELATED APPLICATION

This application claims the benefit or priority under 35 U.S.C. § 119(e) of U.S. Provisional Application Nos. 61/926,063 filed Jan. 10, 2014, the entire contents of which are incorporated herein by this reference.

This application may contain subject matter that is related to that disclosed and claimed in U.S. patent application Ser. No. 12/787,655 filed May 26, 2010, now U.S. Pat. No. 8,961,450 granted on Feb. 24, 2015, the entire contents of which are incorporated herein by this reference.

INCORPORATION BY REFERENCE

This application also includes subject matter that is related to subject matter described in U.S. patent application Ser. No. 13/219,514 filed Aug. 26, 2011, now U.S. Pat. No. 9,061,056 granted on Jun. 23, 2915 and U.S. patent application Ser. No. 09/225,026 filed Jan. 4, 1999, now U.S. Pat. No. 6,183,773 granted on Feb. 6, 2001, each of which are also incorporated herein in its entirety. All publications and patent applications mentioned in this specification are herein incorporated by reference in their entirety to the same extent as if each individual publication or patent application was specifically and individually indicated to be incorporated by reference.

FIELD

This application relates to the timing of subsequent therapy in a light based therapy method.

BACKGROUND

Acne vulgaris is a follicular skin disease that is characterized by the appearance of comedones, papules, nodules, and cysts. Comedones are hair follicles that are blocked with a keratin plug. Open comedones, those in which the keratin plug is visible, form "black heads" and closed comedones form "whiteheads" that often progress to inflamed papules, nodules, and cysts. The presence of bacteria in a follicle attracts white blood cells to the follicle, which can cause an inflammatory response seen as papules (red bumps), pustules, and nodules. Acne may be minor, where only a few comedones or papules are present, or it may be highly inflammatory and leave disfiguring scars. Improved methods of treating or ameliorating follicular skin diseases, such as acne vulgaris, are required.

The mechanism of one type of treatment described herein is through delivery of light absorbing particles in to the sebaceous follicles selectively followed by pulsed laser irradiation that causes selective heating. Cell death occurs primarily due to heat fixation or protein denaturation though some occurs via apoptosis and accidental cell death. It is desired to achieve a high level of injury in one single treatment but without collateral damage and side effects. Due to various reasons including limited delivery of the particles possible in one treatment, the injury is limited and may not lead to complete resolution of acne.

While a single treatment may be a complete treatment, there may be patients or treatment scenarios that would benefit from two or more treatments delivered in such a way as to further enhance the clinical outcome.

SUMMARY OF THE DISCLOSURE

As described below, the present invention provides methods for treating or ameliorating follicular skin diseases (e.g., acne) in a subject (e.g., a human) and compositions comprising energy (e.g., light) absorbing submicron particles (e.g., nanoparticles comprising a silica core and a gold shell) and methods for delivering such particles via topical application into, e.g., a hair follicle, sebaceous duct, and/or sebaceous gland, for use in accordance with those methods.

Thus, in one aspect, the invention provides a method of treating or ameliorating a follicular skin disease in a subject, the method comprising: topically applying a formulation comprising sub-micron particles comprising a light absorbing material to the subject's skin; facilitating delivery of the material into a hair follicle, sebaceous gland, sebaceous gland duct, or infundibulum of the skin by mechanical agitation, acoustic vibration, ultrasound, alternating suction and pressure, or microjets; and exposing the sub-micron particles to energy activation, thereby treating or ameliorating the follicular skin disease in the subject.

In another aspect, the invention provides a method of improving the appearance of enlarged pores in the skin of a subject, the method comprising: topically applying a formulation comprising sub-micron particles comprising a light absorbing materials to the subject's skin; facilitating delivery of the materials to a hair follicle, sebaceous gland, sebaceous gland duct, or infundibulum of the skin by mechanical agitation, acoustic vibration, ultrasound, alternating suction and pressure, or microjets; and exposing the sub-micron particles to energy activation, thereby improving the appearance of enlarged pores in the skin of the subject.

In yet another aspect, the invention provides a method of improving the appearance of oily skin of a subject, the method comprising: topically applying a formulation comprising sub-micron particles comprising a light absorbing materials to the subject's skin; facilitating delivery of the sub-micron particles to a hair follicle, sebaceous gland, sebaceous gland duct, or infundibulum of the skin by mechanical agitation, acoustic vibration, ultrasound, alternating suction and pressure, or microjets; and exposing the sub-micron particles to energy activation, thereby improving the appearance of oily skin of the subject.

Another aspect of the invention provides a method for permanently removing hair of a subject, the method comprising: topically applying a light-absorbing material to the skin of the subject, and exposing the material to energy activation, thereby permanently removing the hair. In one embodiment, the hair is lightly pigmented or thin hair. In another embodiment, the method further comprises epilating hair from the follicle of the subject before topically applying the light-absorbing material to the skin of the subject and exposing the material to energy activation.

In another aspect, the invention provides a method for treating hyperhidrosis by thermally damaging eccrine glands or their surrounding area, the method comprising: topically applying a light-absorbing material to the skin of a subject, and exposing the material to energy activation, thereby permanently removing the glands and treating hyperhidrosis.

In yet another aspect, the invention provides a method of facilitating delivery of a light absorbing material to a target volume within the skin of a subject to achieve a therapeutic effect, the method comprising: topically applying a formulation comprising a light absorbing material to a subject's skin to deliver the material to a reservoir within the skin; facilitating delivery of the material to a target volume within the skin of the subject by irradiating the skin with a first series of light pulses; and exposing the light absorbing material to a second series of light pulses to heat the material and thermally damage the target volume to achieve a therapeutic effect.

In still another aspect, the invention provides a method of facilitating delivery of a light absorbing material to a target volume within the skin of a subject to achieve a therapeutic effect, the method comprising: topically applying a formulation comprising a light absorbing material to a subject's skin; facilitating delivery of the material to a reservoir in the skin by mechanical agitation; facilitating delivery of the material to a target volume within the skin by applying a train of low-energy laser pulses each pulse lasting for a microsecond or less to drive the material into the target volume; and exposing the light absorbing material to a second series of low-energy laser pulses to heat the material and thermally damage the target volume to achieve a therapeutic effect.

Still another aspect of the invention provides a method of treating or ameliorating a follicular skin disease of a subject, the method comprising: topically applying a formulation comprising a sub-micron particle comprising a light absorbing material to a subject's skin; facilitating delivery of the material from the skin into a hair follicle by acoustically created microjets in the formulation; and exposing the sub-micron particle to energy activation, thereby treating the follicular skin disease.

In yet another aspect, the invention provides a method of treating or ameliorating a follicular skin disease of a subject, the method comprising: exposing the subject's skin to a formulation comprising sub-micron particles comprising a light absorbing material; and facilitating delivery of the material from the skin into a hair follicle by low frequency ultrasound induced cavitation within the formulation near the surface of the skin adjacent to the hair follicle; and exposing the sub-micron particles to energy activation, thereby treating the follicular skin disease.

Still another aspect of the invention provides a method of facilitating delivery of a light absorbing material to a target volume within the skin of a subject, the method comprising: topically applying a formulation comprising a light absorbing material to a subject's skin to deliver the material to a reservoir within the target volume of the skin; facilitating delivery of the material to a target volume within the skin of the subject substantially via a transfollicular pathway; and exposing the light absorbing material to a series of light pulses to heat the material and thermally damage the target volume to achieve a therapeutic effect.

In another aspect, the invention provides a method of treating or ameliorating a follicular skin disease of a subject, the method comprising: topically applying a formulation comprising particles of a light absorbing material to a subject's skin; acoustically cavitating the formulation for selectively facilitating delivery of the particles in the formulation into a sebaceous gland primarily through the corresponding hair follicle; and irradiating the particles with light to treat the follicular skin disease.

Another aspect of the invention provides a method of treating or ameliorating a follicular skin disease of a subject, the method comprising: topically applying a formulation comprising sub-micron particles comprising a light absorbing material to a subject's skin; delivering the formulation into one or more sebaceous glands substantially via a transfollicular pathway; and exposing the sub-micron particles to energy activation, thereby treating the follicular skin disease.

Still another aspect of the invention provides a method of treating or ameliorating a follicular skin disease of a subject, the method comprising: topically applying a formulation comprising a sub-micron particle comprising a light absorbing material to a subject's skin; facilitating delivery of the material into a hair follicle by low frequency ultrasound induced cavitation near the surface of the skin adjacent to the hair follicle; and treating or ameliorating the follicular skin disease adjacent to the sub-micron particle using heat produced by irradiating the sub-micron particle with light.

The above-described method aspects of the invention or other aspects of the invention described herein include a plurality of useful embodiments that are universally applicable to the methods of the invention described herein.

Thus, in one embodiment, delivery of the light absorbing material into, e.g., the hair follicle, is facilitated by ultrasound-created microjets within the formulation.

In another embodiment, the sub-micron particles to energy activation comprises irradiating the sub-micron particle with light, thereby heating the particle.

In another embodiment, the sub-micron particles are within a sebaceous gland during irradiation. In one embodiment, the sub-micron particles are substantially completely within the sebaceous gland during irradiation. In another embodiment, the sub-micron particles are within a sebaceous gland duct during irradiation. In yet another embodiment, the sub-micron particles are substantially completely within the sebaceous gland duct during irradiation. In still another embodiment, the sub-micron particles are within an infundibulum involved in the follicular skin disease.

In certain embodiments, the light absorbing material in the formulation comprises a photoactive compound, photodynamic therapy (PDT) pro-drug or PDT drug.

In one embodiment, the application of ultrasound is at a frequency in the range of 20 kHz to 500 kHz. In another embodiment, the application of ultrasound is at a frequency in the range of 20 kHz to 100 kHz. In yet another embodiment, the application of ultrasound is at a frequency in the range of 20 kHz to 60 kHz. In still another embodiment, the application of ultrasound energy is at a frequency in the range of 30 kHz to 50 kHz.

In one embodiment, the ultrasound power density is from about 0.5-50 W/cm2. In another embodiment, the ultrasound horn face peak-to-peak amplitude displacement is in the range of 0.5 to 30 microns.

In certain embodiments, the particles or light absorbing materials are sized to enter into and along a follicle pore. In one embodiment, the particles are sized from about 1 micron to about 5 microns. In another embodiment, the particles are between about 50 nm about 250 nm in diameter. In yet another embodiment, the particles are nanoshells.

In certain other embodiments, the sizes of sub-micron particles according to the invention are selected for passage through the hair follicle and into a sebaceous gland of the hair follicle. In one embodiment, the hair follicle is a terminal follicle. In another embodiment, the hair follicle is a vellus follicle. In yet another embodiment, the hair follicle is a sebaceous follicle.

In one embodiment, the sub-micron particle size is between about 0.01 microns to about 1.0 microns. In another embodiment, the sub-micron particle size is between about 0.05 to about 0.25 microns.

In one embodiment, the facilitating step further comprises selecting characteristics for the ultrasound-created microjets to create bubbles in the formulation about the same size as the hair follicle pore. In another embodiment, the facilitating step further comprises selecting characteristics for low frequency ultrasound induced cavitation for creating bubbles in the formulation about the same size as the hair follicle.

In other embodiments, the ultrasound-created microjets in the formulation are within about 50 microns to about 100 microns of the surface of the skin of the subject.

In certain embodiments, delivery of the light absorbing matter is facilitated by an immersion cavitation step. In one embodiment, the facilitating step produces cavitation within about 50-100 microns of the surface of the skin. In another embodiment, the portion of the stratum corneum of the portion of the subject's skin exposed to the delivery step remains intact In certain other embodiments, delivery, e.g., substantially via a transfollicular pathway, of the light absorbing material into, e.g., one or more sebaceous glands or hair follicles, is facilitated by low frequency ultrasound induced cavitation near the surface of the skin adjacent to the hair follicle. In one embodiment, the induced cavitation is between about 50 microns to about 100 microns from the surface of the skin. In another embodiment, the characteristics of the low frequency ultrasound are selected such that the induced cavitation near the surface of the skin leaves the stratum corneum intact.

In one embodiment, the follicular disease for treatment is hyperhidrosis. In certain embodiments, the facilitating step delivers particles into an eccrine gland via the eccrine gland duct.

In other embodiments, the follicular disease for treatment is acne vulagris. In yet other embodiments, the follicular disease for treatment is sebaceous hyperplasia In still other embodiments, the follicular disease for treatment is hirsuteness.

In one embodiment, the sub-micron particles are coated with PEG. In another embodiment the particles have an absorption peaked between 700 and 1,100 nm wavelength of light. In another embodiment, the sub-micron particles have a ratio of the shell diameter to the core diameter between about 1.05 to about 2.0.

In another embodiment, the sub-micron particle is a nanoparticle or nanoshell. In certain embodiments, the nanoparticle or nanoshell has a diameter of about 50 to about 300 nm (e.g., 50, 75, 100, 125, 150, 175, 200, 250, 300 nm). In one embodiment, the nanoparticle or nanoshell has a diameter of about 50 to about 250 nm. In another embodiment, the nanoparticle has a diameter of about 150 nm.

In another embodiment, the nanoparticle is coated with PEG.

In yet another embodiment, the nanoparticle is a nanoshell. In certain embodiments, the nanoparticle comprises a silica core and a gold shell.

In certain embodiments, the sub-micron particles comprise from about 0.5% to about 2% of the formulation. In one embodiment, the formulation comprises about 0.5 to about 2% of a suspension comprising nanoparticles. In another embodiment, the formulation comprises about 0.1 to about 10% of a suspension comprising nanoparticles.

In one embodiment, the formulation contains a surfactant and/or is hydrophilic. In another embodiment, the formulation contains a surfactant and/or is lipophilic. In yet another embodiment, the formulation contains a surfactant and/or is liposomal. In certain embodiments, the surfactant is less than 10% of the formulation.

In certain embodiments, the formulation comprises a component having ability to solubilize lipids. In one embodiment, the component is ethanol.

In one embodiment, the formulation comprises one or more of ethanol, isopropyl alcohol, propylene glycol, a surfactant, and/or isopropyl adipate. In another embodiment, the formulation comprises hydroxypropylcellulose (HPC) and carboxymethyl cellulose (CMC). In still another embodiment, the formulation comprises any one or more of water, ethanol, propylene glycol, polysorbate 80, diisopropyl adipate, phospholipon, and thickening agents.

In certain embodiments, the formulation has an optical density of between 5-500. In one embodiment, the formulation has an optical density of about 75. In another embodiment, the formulation has an optical density of about 125. In another embodiment, the formulation has an optical density of about 250.

In certain embodiments, energy activation, e.g., light activation, is accomplished with a pulsed laser light that delivers light energy at a wavelength that is absorbed by the particle. In one embodiment, the pulsed laser light delivers light energy at a wavelength that is preferentially absorbed by the particle. In another embodiment, energy activation is accomplished with a continuous laser that delivers light energy at a wavelength that is absorbed by the particle In one embodiment, the light energy has a wavelength range from about 700 to about 1,100 nm. In another embodiment, the light energy has a fluence of less than about 100 J/cm$^2$. In still another embodiment, the light energy has a pulse duration of from about 0.5 ms-1,000 ms.

In certain embodiments, the skin is prepared for the method by heating, by removing the follicular contents, and/or by epilation. In one embodiment, the follicular contents are removed by a method comprising contacting the follicle pore with adhesive polymers.

In certain other embodiments, the topically applied sub-micron particles are wiped from the skin prior to energy activation. In one embodiment, the topically applied sub-micron particles are wiped from the skin with the aid of a fluid, prior to application of optical radiation. In another embodiment, the fluid is water, ethanol or acetone. In another embodiment, the fluid can be comprised of one or more of water, solvents, surfactants, alcohols.

In certain other embodiments, the skin is heated before, during, or after topical application to a temperature sufficient to assist in follicular delivery. In one embodiment, the heating is accomplished via ultrasound. In another embodiment, the heating is accomplished via steam. In yet another embodiment, the heating is accomplished via hot packs. In still another embodiment, heating is accomplished via hot towels. In general, the heating is not sufficient to cause pain, tissue damage, burns, or other heat-related effects in the skin. In one embodiment, the temperature is about 35-44° C. In another embodiment, the temperature is about 40-44° C. In yet another embodiment, the temperature is about 42° C.

In certain embodiments, the step of exposing further comprises placing a volume of the formulation in a container so that the formulation is in contact with the subject's skin. In one embodiment, the step of facilitating further comprises placing an ultrasound applicator into the container and immersed in the formulation.

In one embodiment, the target volume is the sebaceous gland, the target volume is within the follicle beneath the skin.

In another aspect, the invention provides a composition comprising a cosmetically acceptable carrier and a plurality of plasmonic nanoparticles in an amount effective to induce thermomodulation in a target tissue region with which the composition is topically contacted.

In one embodiment, the plasmonic nanoparticles are activated by exposure to energy delivered from a nonlinear excitation surface plasmon resonance source to the target tissue region. In another embodiment, the plasmonic nanoparticle comprises a metal, metallic composite, metal oxide, metallic salt, electric conductor, electric superconductor, electric semiconductor, dielectric, quantum dot or composite from a combination thereof. In yet another embodiment, a substantial amount of the plasmonic particles present in the composition comprise geometrically-tuned nanostructures.

In one embodiment, the plasmonic particles comprise any geometric shape currently known or to be created that absorb light and generate plasmon resonance at a desired wavelength, including nanoplates, solid nanoshells, hollow nanoshells, nanorods, nanorice, nanospheres, nanofibers, nanowires, nanopyramids, nanoprisms, nanostars or a combination thereof. In another embodiment, the plasmonic particles comprise silver, gold, nickel, copper, titanium, silicon, galadium, palladium, platinum, or chromium.

In one embodiment, the cosmetically acceptable carrier comprises an additive, a colorant, an emulsifier, a fragrance, a humectant, a polymerizable monomer, a stabilizer, a solvent, or a surfactant. In one particular embodiment, the surfactant is selected from the group consisting of sodium laureth 2-sulfate, sodium dodecyl sulfate, ammonium lauryl sulfate, sodium octech-1/deceth-1 sulfate, lipids, proteins, peptides or derivatives thereof. In another specific embodiment the surfactant is present in the composition in an amount between about 0.1 and about 10.0% weight-to-weight of the carrier.

In one embodiment, the solvent is selected from the group consisting of water, propylene glycol, alcohol, hydrocarbon, chloroform, acid, base, acetone, diethyl-ether, dimethyl sulfoxide, dimethylformamide, acetonitrile, tetrahydrofuran, dichloromethane, and ethylacetate.

In another embodiment, the composition comprises plasmonic particles that have an optical density of at least about 1 O.D. at one or more peak resonance wavelengths.

In yet another embodiment, the plasmonic particles comprise a hydrophilic or aliphatic coating, wherein the coating does not substantially adsorb to skin of a mammalian subject, and wherein the coating comprises polyethylene glycol, silica, silica-oxide, polyvinylpyrrolidone, polystyrene, a protein or a peptide.

In one embodiment, the thermomodulation comprises damage, ablation, lysis, denaturation, deactivation, activation, induction of inflammation, activation of heat shock proteins, perturbation of cell-signaling or disruption to the cell microenvironment in the target tissue region.

In another embodiment, the target tissue region comprises a sebaceous gland, a component of a sebaceous gland, a sebocyte, a component of a sebocyte, sebum, or hair follicle infundibulum.

In a specific embodiment, the target tissue region comprises a bulge, a bulb, a stem cell, a stem cell niche, a dermal papilla, a cortex, a cuticle, a hair sheath, a medulla, a pylori muscle, a Huxley layer, or a Henle layer.

In another aspect, the invention provides a method for performing targeted ablation of a tissue to treat a mammalian subject in need thereof, comprising the steps of i) topically administering to a skin surface of the subject a composition of the invention as described above; ii) providing penetration means to redistribute the plasmonic particles from the skin surface to a component of dermal tissue; and iii) causing irradiation of the skin surface by light.

In one embodiment, the light source comprises excitation of mercury, xenon, deuterium, or a metal-halide, phosphorescence, incandescence, luminescence, light emitting diode, or sunlight.

In another embodiment, the penetration means comprises high frequency ultrasound, low frequency ultrasound, massage, iontophoresis, high pressure air flow, high pressure liquid flow, vacuum, pre-treatment with fractionated photothermolysis or dermabrasion, or a combination thereof.

In yet another embodiment, the irradiation comprises light having a wavelength of light between about 200 nm and about 10,000 nm, a fluence of about 1 to about 100 joules/$cm^2$, a pulse width of about 1 femtosecond to about 1 second, and a repetition frequency of about 1 Hz to about 1 THz.

In another aspect, the invention provides a composition comprising a cosmetically acceptable carrier, an effective amount of sodium dodecyl sulfate, and a plurality of plasmonic nanoparticles in an amount effective to induce thermal damage in a target tissue region with which the composition is topically contacted, wherein the nanoparticles have an optical density of at least about 1 O.D. at a resonance wavelength of about 810 nanometers or 1064 nanometers, wherein the plasmonic particles comprise a silica coating from about 5 to about 35 nanometers, wherein the acceptable carrier comprises water and propylene glycol.

In still another aspect, the invention provides a system for laser ablation of hair or treatment of acne comprising a composition of the invention as described above and a source of plasmonic energy suitable for application to the human skin.

The desired effects from selective photothermolysis of sebaceous glands using one or a combination of the above can be enhanced by choosing an optimal treatment interval. In one aspect, the treatment interval is selected by re-treating cells and tissue when they are most vulnerable to repeated thermal injury. In one aspect, the second or subsequent treatment occurs one, two, three, four, five or six days after the initial or just prior treatment. In one aspect, the interval between second and subsequent or the just prior treatment is the same or, optionally, different. In one aspect, the timing between second or subsequent treatment is during a window of 4-14 days since the last treatment.

The invention provides compositions, methods and systems for treating follicular skin diseases during a single treatment or using two or more treatments at a desired treatment interval. Compositions and articles defined by the invention were isolated or otherwise manufactured in connection with the examples provided below. Other features and advantages of the invention will be apparent from the detailed description, and from the claims.

DETAILED DESCRIPTION

Figure 1:
FIG. 1 is a micrograph showing thermal damage to the follicular epithelium and part of the sebaceous gland following delivery of a nanoshell suspension by massage.

The invention features compositions comprising light/energy absorbing materials and methods that are useful for their topical delivery to a target (e.g., a follicle, follicular infundibulum, sebaceous gland) for the treatment of a follicular disease.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "ameliorate" is meant decrease, suppress, attenuate, diminish, arrest, or stabilize the development or progression of a skin disease or condition. One exemplary skin condition is acne vulgaris The terms "compounds" and "materials" are used interchangeably and refer to o active moieties in accordance with the invention.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "energy activation" is meant stimulation by an energy source that causes thermal or chemical activity. Energy activation may be by any energy source known in the art. Exemplary energy sources include a laser, ultrasound, acoustic source, flashlamp, ultraviolet light, an electromagnetic source, microwaves, or infrared light. An energy absorbing material absorbs the energy and become thermally or chemically active.

The terms "light", "light energy", "optical energy" and "optical radiation" are used interchangeable herein.

As used herein, "obtaining" as in "obtaining an agent" includes synthesizing, purchasing, or otherwise acquiring the agent.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting an energy activatable material of the present invention within or to the subject such that it can performs its intended function. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Preferred carriers include those which are capable of entering a pore by surface action and solvent transport such that the energy activatable material is carried into or about the pore, e.g., into the sebaceous gland, to the plug, into the infundibulum and/or into the sebaceous gland and infundibulum.

By "reduces" is meant a negative alteration of at least 10%, 25%, 50%, 75%, or 100%.

By "reference" is meant a standard or control condition.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Follicular Disease Pathogenesis

Sebaceous glands are components of the pilosebaceous unit. They are located throughout the body, especially on the face and upper trunk, and produce sebum, a lipid-rich secretion that coats the hair and the epidermal surface. Sebaceous glands are involved in the pathogenesis of several diseases, the most frequent one being acne vulgaris. Acne is a multifactorial disease characterized by the occlusion of follicles by plugs made out of abnormally shed keratinocytes of the infundibulum (upper portion of the hair follicle) in the setting of excess sebum production by hyperactive sebaceous glands.

The infundibulum is an important site in the pathogenesis of many follicular diseases (e.g., acne). There is evidence that abnormal proliferation and desquamation of infundibular keratinocytes leads to the formation of microcomedones and, subsequently, to clinically visible follicular "plugs" or comedones. Because the architecture of the infundibulum is important in the pathogenesis of acne, the selective destruction of this portion of the follicle through energy activatable material-assisted energy, e.g., laser, targeting eliminates or reduces the site of pathology.

Topical Delivery of Light/Energy Absorbing Materials

The invention provides delivery of light/energy absorbing materials via topical application into skin appendages of the follicle, specifically follicular infundibulum and the sebaceous gland. In one embodiment, such materials are useful for the treatment of follicular diseases, such as acne (e.g., acne vulgaris), hyperhidrosis. The introduction of energy activatable materials in sebaceous glands followed by exposure to energy (light) with a wavelength that corresponds to the absorption peak of the chromophore will increase the local absorption of light in tissue and lead to selective thermal damage of sebaceous glands.

In another aspect, there is a treating of hyperhidrosis by thermally damaging eccrine glands or their surrounding area by applying a light-absorbing material to the skin of a subject, facilitating delivery into an eccrine gland via the eccrine gland duct and exposing said material to energy activation. The method thereby permanently removes the glands. In one aspect, the method of treating a follicular disease is for treatment of hyperhidrosis.

Skin Preparation

If desired, the skin is prepared by one or a combination of the following methods. Delivery of light absorbing materials may be facilitated by epilation of hair, which is performed prior to topical application of the light absorbing materials.

Optionally, the skin is degreased prior to application of the light absorbing compounds. For example, acetone wipes are used prior to application of sebashells to degrease the skin, especially to remove the sebum and follicular contents.

For certain subjects, delivery may be facilitated by reducing or clearing clogged follicles prior to application of the light absorbing material. Such clearing can enhance the delivery of the plasmonic nanoshells. The follicles, especially in acne prone patients, are clogged by shed keratinocytes, sebum, and bacteria P. acnes. The follicle can be emptied by application of vacuum. Other methods are cyanoacrylate stripping, strips with components such as Polyquaternium 37 (e.g., BIORE pore removal strips). The polymers flow into the follicle and dry over time. When the dry polymer film is pulled out, the follicular contents are pulled out, emptying the follicle.

Optionally, the skin may be heated prior to application of the light absorbing materials. Heating reduces the viscosity of the sebum and may liquefy components of the sebum. This can facilitate delivery of light absorbing materials (e.g., formulated as nanoshells) to the follicle.

Topical Delivery of Light Absorbing Materials

Light absorbing materials, such as non-toxic dyes (e.g., indocyanine green or methyelene blue) are topically applied to the skin following any desired preparation. The topically applied formulations containing the light absorbing materials may comprise ethanol, propylene glycol, surfactants, and acetone. Such additional components facilitate delivery into the follicle.

Delivery of light absorbing materials is facilitated by application of mechanical agitation, such as massage, acoustic vibration in the range of 10 Hz-20 kHz, ultrasound, alternating suction and pressure, and jets. In one embodiment, light absorbing materials are delivered as nanoparticles, such as nanoshells or nanorods that absorb light in the visible and the near-IR region of the electromagnetic spectrum. In another embodiment, light absorbing materials are quantum dots. Preferably, the light absorbing materials are formulated for topical delivery in a form that facilitates follicular delivery. In one embodiment, such formulations comprise water, ethanol, isopropyl alcohol, propylene glycol, surfactants, and isopropyl adipate and related compounds. In one embodiment, the formulation is hydrophilic and contains a surfactant. In another embodiment, the formulation is lipophilic and contains a surfactant. In still another embodiment, the composition is liposomal and contains a surfactant. In any of the above embodiments, the surfactant is less than 10% of the formulation. In another embodiment, the formulation is hydrophilic. In still another embodiment, the formulation is lipophilic. In still another embodiment, composition is liposomal.

Ultrasound Facilitated Delivery

Ultrasound has been used to achieve transdermal delivery of compounds into the body. Ultrasound appears to generate shock-waves and micro-jets resulting from bubble cavitation that causes the formation of channels in the skin, which provide for the transport of molecules of interest. Previous efforts have been directed toward the delivery of the compounds through the stratum corneum. Small molecules, for example, with sizes less than 5 nm, can be delivered through the stratum corneum. The delivery rate through the stratum corneum goes down significantly as particle size increases. For example, for particles with size of 50 nm and higher, the delivery rate through the stratum corneum is very low. However, this size is still much smaller than the pore opening and the infundibulum of a follicle. For example, 150 nm size silica-core and gold shell structures are being used that are much smaller than the infundibular diameter while showing low deposition in skin through the stratum corneum.

These findings provide the basis of acne treatment in which the infundibulo-sebaceous unit is selectively targeted for first delivery of light absorbing material of appropriate size and then selective thermal damage to the unit with pulsed laser irradiation. Here, ultrasound specifically facilitates the delivery of a light absorbing material into the follicular structure. The shock waves, microjet formation, and streaming deliver the light absorbing particles into the follicular infundibulum and the associated sebaceous gland duct and the sebaceous gland.

Ultrasound is often be accompanied by heating of the target organ, skin. Some heating, for example, up to about 42° C. may help in follicular delivery. However, excessive heating is undesirable, causing pain, tissue damage, and burns. In one embodiment, excessive heating can be avoided by cooling the skin, for example. In another embodiment, the topically applied formulation or a coupling gel can be pre- or parallel-cooled. A low duty cycle with repeated ultrasound pulse bursts can also be used to avoid excessive heating, where during the off-time, the body cools the skin that is being subjected to ultrasound energy.

In certain embodiments, the invention provides two methods of ultrasound delivery are suggested. One is "contact ultrasound" and another is "immersion ultrasound".

In accordance with an embodiment of the contact ultrasound method, a formulation of the invention is topically applied to the skin by spreading into a thin layer and a horn vibrating at an ultrasound frequency is brought into close contact with the formulation-covered skin.

In accordance with an embodiment of the immersion ultrasound method, a reservoir filled with the formulation is placed on top of the skin, a horn is immersed in it without the horn touching the skin at a distance ranging from about 2 mm to about 30 mm, and the horn is then vibrated at ultrasound frequency.

Acoustic cavitation is often an effect observed with ultrasound in liquids. In acoustic cavitation, a sound wave imposes a sinusoidally varying pressure upon existing cavities in solution. During the negative pressure cycle, the liquid is pulled apart at 'weak spots'. Such weak spots can be either pre-existing bubbles or solid nucleation sites. In one embodiment, a bubble is formed which grows until it reaches a critical size known as its resonance size (Leong et al., Acoustics Australia, 2011—acoustics.asn.au, THE FUNDAMENTALS OF POWER ULTRASOUND—A REVIEW, p 54-63). According to Mitragotri (Biophys J. 2003; 85(6): 3502-3512), the spherical collapse of bubbles yields high pressure cores that emit shock waves with amplitudes exceeding 10 kbar (Pecha and Gompf, Phys. Rev. Lett. 2000; 84:1328-1330). Also, an aspherical collapse of bubbles near boundaries, such as skin yields microjets with velocities on the order of 100 m/s (Popinet and Zaleski, 2002; J. Fluid. Mech. 464:137-163). Such bubble-collapse phenomena can assist in delivery of materials into skin appendages, such as hair and sebaceous follicles. Thus, various embodiments of the invention provide for immersion ultrasound methods for optimizing bubble size before collapse to promote efficient delivery of light absorbing materials into the intended target (e.g., sebaceous glands, hair follicles).

The resonance size of the bubble depends on the frequency used to generate the bubble. A simple, approximate relation between resonance and bubble diameter is given by F (in Hz).times.D (in m)=6 mHz, where F is the frequency in Hz and D is the bubble diameter (size) in m. In practice, the diameter is usually smaller than the diameter predicted by this equation due to the nonlinear nature of the bubble pulsation.

Table 1 below gives the size of the resonance size of the bubble as a function of frequency, calculated from the above relationship.

TABLE 1

| F, kHz | 10 | 20 | 30 | 40 | 50 | 100 | 200 | 300 | 400 | 500 | 1,000 |
|---|---|---|---|---|---|---|---|---|---|---|---|
| D_microns | 600 | 300 | 200 | 150 | 120 | 60 | 30 | 20 | 15 | 12 | 6 |

Computer simulations of bubble oscillations give more accurate estimates of the bubble size. For example, in work by Yasui (J. Acoust. Soc. Am. 2002; 112: 1405-1413), three frequencies were investigated in depth. The sizes for single bubble sonoluminescing (SBSL) stable bubbles are lower and ranges are given in the Table 2 below (estimated from FIGS. 1, 2, and 3 of Yasui, 2002):

TABLE 2

| | F, kHz | | |
|---|---|---|---|
| | 20 | 140 | 1,000 |
| D_microns | 0.2-200 | 0.6-25 | 0.2-6 |

For efficient delivery into the follicles with cavitation bubbles, there is an optimal cavitation bubble size range. Strong cavitational shock waves are needed, which are generated with relatively large bubbles. However, if the bubble size is too large, it produces strong shock waves, which may compress the skin, reducing the pore size, and reducing efficient delivery to a target (e.g., sebaceous gland, follicle). For example, if the bubble size is much larger than the follicle opening, the resulting shock waves compress not only the pore opening, but also the skin surrounding the pore opening. This inhibits efficient delivery into the follicle opening. Desirably, bubble sizes should be about the same size as the target pore. Typical pore sizes of follicles on human skin are estimated to be in the range of 12-300 microns. Thus, an advantageous ultrasound frequency range is 20 kHz to 500 kHz. In other alternatives, the application of ultrasound frequency is in the range of 20 kHz to 100 kHz, or 20 kHz to 60 kHz or even 30 kHz to 50 kHz. The desired power density is estimated to be in the range of 0.5-50 W/cm$^2$. This is sufficient to generate cavitation bubbles in the desired size range.

"Immersion cavitation" as used herein is defined as formation and collapse of cavitation bubbles due to the ultrasound energy within the fluid formulation.

In light of the above description, there is also provided a method of facilitating delivery of light absorbing materials into a hair follicle by selecting characteristics for the acoustically created microjets to create bubbles in the formulation about the same size as the hair follicle pore. Selecting the characteristics permits the bubbles to be about the same size as a terminal follicle, a vellus follicle, or a sebaceous follicle. In another alternative implementation in light of the above description, there is also provided a method of facilitating delivery of light absorbing materials into a hair follicle by selecting characteristics for the low frequency ultrasound induced cavitation for creating bubbles in the formulation about the same size as the hair follicle. In one implementation, the hair follicle is a terminal follicle. In another implementation, the hair follicle is a vellus follicle. In still another implementation, the hair follicle is a sebaceous follicle. In still other aspects the ultrasound created microjects or low frequency ultrasound induced cavitation occurs in the formulation between about 50 microns to about 100 microns of the surface of the skin.

In another embodiment, there is also provided a method of treating or ameliorating a follicular skin disease of a subject. The method includes the step of exposing the subject's skin to a formulation comprising a sub-micron particle comprising a light absorbing material to a subject's skin. Next, there is a step of facilitating delivery of said material from the skin into a hair follicle by low frequency ultrasound induced cavitation within the formulation near the surface of the skin adjacent to the hair follicle. Thereafter, exposing said sub-micron particle to energy activation, thereby treating the follicular skin disease. In one alternative, there is also a step of exposing by placing a volume of the formulation in a container so that the formulation is in contact with the subject's skin. Still further, there is also a step of facilitating the method by placing an ultrasound applicator into the container and immersed in the formulation.

In still another embodiment, there is provided a method of facilitating delivery of a light absorbing material to a target volume within the skin of a subject. The method includes the step of topically applying a formulation comprising a light absorbing material to a subject's skin to deliver the material to a reservoir within the target volume of the skin. Next, there is a step of facilitating delivery of said material to a target volume within the skin of the subject substantially via a transfollicular pathway. Next, there is a step of exposing the light absorbing material to a series of light pulses to heat the material and thermally damage the target volume to achieve a therapeutic effect. In one alternative, the formulation has an optical density of between 5-500. In another alternative, the formulation has an optical density of about 75. In still another alternative, the formulation has an optical density of about 125. In still another alternative, the formulation has an optical density of about 250. In one aspect, the target volume is the sebaceous gland. In another aspect, the target volume is within the follicle beneath the skin.

In still another aspect, the facilitating step includes an immersion cavitation step. In another alternative, there is provided a step of facilitating delivery into a sebaceous gland using immersion ultrasound. In one alternative, the facilitating step includes forming microjets within the formulation. In one aspect, the facilitating using ultrasound produces cavitation within a formulation and about 50 to 100 microns of the surface of the skin. In any of the above described methods, there is also the step of acoustically cavitating the formulation for selectively facilitating delivery of said particles in the formulation into a sebaceous gland primarily through the corresponding hair follicle. Thereafter, there is the step of irradiating said particles with light to treat the follicular skin disease. In one embodiment, the particles are sized from about 1 micron to about 5 microns. In another aspect, the particles are sized to enter into and along a follicle pore. In still other embodiments, the particles are between about 50 nm about 250 nm in diameter. In another embodiment, the particles are nanoshells.

Energy (Light) Activation

After the topical application and facilitated delivery (e.g., by mechanical agitation, ultrasound), the top of the skin is wiped off to remove the residual light absorbing material. This is followed by energy (light) irradiation. The light is absorbed by the material inside the follicle or sebaceous gland leading to localized heating. The light source depends on the absorber used. For example, for nanoshells that have broad absorption spectrum tuned to 800 nm resonance wavelength, sources of light such as 800-nm, 755-nm, 1,064-nm or intense pulsed light (IPL) with proper filtering can be used. In one aspect, the nanoparticles in a suspension have a peak absorption between 700 and 1,100 nm wavelength of light. Such pulsed laser irradiation leads to thermal damage to the tissue surrounding the material. In one aspect, the light energy has a fluence of less than about 100 J/cm2. Damage to infundibular follicular stem cells and/or sebaceous glands leads to improvement in the follicular conditions, such as acne. Such methods can be used not only for particulates in suspensions but for small dissolved molecules in solution as well. These can include pharmaceutical drugs, photodynamic therapy (PDT) pro-drugs, or PDT drugs.

Suitable energy sources include light-emitting diodes, incandescent lamps, xenon arc lamps, lasers or sunlight. Suitable examples of continuous wave apparatus include, for example, diodes. Suitable flash lamps include, for example pulse dye lasers and Alexandrite lasers. Representative lasers having wavelengths strongly absorbed by chromophores, e.g., laser sensitive dyes, within the epidermis and infundibulum but not sebaceous gland, include the short-pulsed red dye laser (504 and 510 nm), the copper vapor laser (511 nm) and the Q-switched neodymium (Nd): YAG laser having a wavelength of 1064 nm that can also be frequency doubled using a potassium diphosphate crystal to produce visible green light having a wavelength of 532 nm. In the present process, selective photoactivation is employed whereby an energy (light) source, e.g., a laser, is matched with a wave-length to the absorption spectrum of the selected energy activatable material, preferably a chromophoric agent.

It is easier to achieve a high concentration of the light absorbing material in the infundibulum than the sebaceous duct and the gland, which provide a higher resistance to material transport. The follicle including the sebaceous gland can be irreversibly damaged just relying on light absorption principally but the material in the infundibulum. This is mediated through damage to the keratinocytes in the follicular epithelium. Also, with higher energy pulses can be used to extend the thermal damage to include the stem cells in the outer root sheath, the bulge, as well as the outside periphery of the sebaceous glands. However, such high energy should not lead to undesired side effects. Such side effects can be mitigated by use of cooling of the epidermis and also use of longer pulse durations, on the order of several milliseconds, extending up to 1,000 ms.

Thermal alteration of the infundibulum itself with only limited involvement of sebaceous glands may improve acne. Appearance of enlarged pores on the face is a common issue for many. This is typically due to enlarged sebaceous glands, enlarged infundibulum, as well as enlarged pore opening. Heating of tissue, especially collagen, shrinks the tissue. The delivery of nanoshells and thermal targeting of the same in the infundibulo-sebaceous unit that includes the upper, lower infundibulum, as well as the sebaceous gland, will improve the appearance of enlarged pores.

Energy Absorbing Material Formulations

The invention provides compositions comprising light/energy absorbing materials for topical delivery. In one embodiment, a particle in the composition is a nanoparticle comprising a silica core and a gold shell. In still another embodiment, a compound of the invention comprises a silica core and a gold shell (150 nm). In another embodiment, nanoshells used are composed of a 120 nm diameter silica core with a 15 micron thick gold shell, giving a total diameter of 150 nm.

The nanoshell is covered by a 5,000 MW PEG layer. The PEG layer prevents and/or reduces nanoshell aggregation, thereby increasing the nanoshell suspensions stability and shelf-life. In one embodiment, the nanoparticle has a diameter of about 50 to about 250 nm. In some embodiments, the ratio of the shell diameter to the core diameter of the particles used herein are between about 1.5 to about 2.0. In another aspect, the particles in a formulation comprise from about 0.5% to about 2% of the formulation.

Nanoparticles of the invention exhibit Surface Plasmon Resonance, such that Incident light induces optical resonance of surface plasmons (oscillating electrons) in the metal. The Wavelength of peak absorption can be "tuned" to the near-infrared (IR) portion of the electromagnetic spectrum. The submicron size of these nanoparticles allows their entry into the infundibulum, sebaceous duct and sebaceous gland of the epidermis, and minimizes their penetration of the stratum corneum. In particular embodiment, selective transfollicular penetration of nanoparticles ~150-350 nm in diameter is achieved. In one aspect, there is provided a method of treating or ameliorating a follicular skin disease of a subject. There is a step of topically applying a formulation comprising a sub-micron particle comprising a light absorbing material to a subject's skin. Next there is a step of delivering said formulation into one or more sebaceous glands substantially via a transfollicular pathway. Next, there is a step of exposing said sub-micron particle to energy activation, thereby treating the follicular skin disease. In one aspect, a portion of the stratum corneum within the portion of the skin exposed to the delivering step remains intact. Still further, the delivering step is completed using an immersion ultrasound step whereby the portion of the stratum corneum within the portion of the skin exposed to the delivering step remains intact.

If desired, light/energy absorbing materials are provided in vehicles formulated for topical delivery. In one embodiment, a composition of the invention is formulated with agents that enhance follicular delivery, including but not limited to, one or more of ethanol, isopropyl alcohol, propylene glycols, surfactants such as polysorbate 80, Phospholipon 90, polyethylene glycol 400, and isopropyl adipate. In other embodiments, a composition of the invention is formulated with one or more thickening agents, including but not limited to, hydroxypropylcellulose (HPC) and carboxymethyl cellulose (CMC), to enhance handling of the formulations.

Wetting agents, emulsifiers and lubricants, such as sodium lauryl sulfate and magnesium stearate, as well as coloring agents, release agents, coating agents, sweetening and perfuming agents, preservatives and antioxidants can also be present in the compositions.

Liquid dosage forms for topical administration of the compositions of the invention include pharmaceutically acceptable emulsions, microemulsions, solutions, creams, lotions, ointments, suspensions and syrups. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, peach, almond and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. The term "cream" is art recognized and is intended to include semi-solid emulsion systems which contain both an oil and water. Oil in water creams are water miscible and are well absorbed into the skin, Aqueous Cream BP. Water in oil (oily) creams are immiscible with water and, therefore, more difficult to remove from the skin. These creams are emollients, lubricate and moisturize, e.g., Oily Cream BP. Both systems require the addition of either a natural or a synthetic surfactant or emulsifier.

The term "ointment" is art recognized and is intended to include those systems which have oil or grease as their continuous phase. Ointments are semi-solid anhydrous substances and are occlusive, emollient and protective. Ointments restrict transepidermal water loss and are therefore hydrating and moisturizing. Ointments can be divided into two main groups—fatty, e.g., White soft paraffin (petrolatum, Vaseline), and water soluble, e.g., Macrogol (polyethylene glycol) Ointment BP. The term "lotion" is art recognized and is intended to include those solutions typically used in dermatological applications. The term "gel" is art recognized and is intended to include semi-solid permutations gelled with high molecular weight polymers, e.g., carboxypolymethylene (Carbomer BP) or methylcellulose, and can be regarded as semi-plastic aqueous lotions. They are typically non-greasy, water miscible, easy to apply and wash off, and are especially suitable for treating hairy parts of the body.

Subject Monitoring

The disease state or treatment of a subject having a skin disease or disorder can be monitored during treatment with a composition or method of the invention. Such monitoring may be useful, for example, in assessing the efficacy of a particular agent or treatment regimen in a patient. Therapeutics that promote skin health or that enhance the appearance of skin are taken as particularly useful in the invention.

Kits

The invention provides kits for the treatment or prevention of a skin disease or disorder, or symptoms thereof. In one embodiment, the kit includes a pharmaceutical pack comprising an effective amount of a light/energy absorbing material (e.g., a nanoshell having a silica core and a gold shell (150 nm)). Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having or at risk of developing a skin disease or disorder. The instructions will generally include information about the use of the compositions for the treatment or prevention of a skin disease or disorder. In other embodiments, the instructions include at least one of the following: description of the compound or combination of compounds; dosage schedule and administration for treatment of a skin condition associated with acne, dermatitis, psoriasis, or any other skin condition characterized by inflammation or a bacterial infection, or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

The following examples are provided to illustrate the invention, not to limit it. those skilled in the art will understand that the specific constructions provided below may be changed in numerous ways, consistent with the above described invention while retaining the critical properties of the compounds or combinations thereof.

Laser Hair Removal

The invention features compositions and methods that are useful for laser hair removal, particularly in light colored hair. In laser hair removal, a specific wavelength of light and pulse duration is used to obtain optimal effect on a targeted tissue with minimal effect on surrounding tissue. Lasers can cause localized damage to a hair follicle by selectively heating melanin, which is a dark target material, while not heating the rest of the skin. Because the laser targets melanin, light colored hair, gray hair, and fine or thin hair, which has reduced levels of melanin, is not effectively targeted by existing laser hair removal methods. Efforts have been made to deliver various light absorbing materials, such as carbon particles, extracts from squid ink, known commercially as meladine, or dyes into the follicle. These methods have been largely ineffective.

The present invention provides microparticles in a suspension form that is topically applied after skin preparation as delineated herein above. In particular, the skin is prepared by epilation of the hair shaft and light absorbing materials are delivered to the hair follicle. Preferably, the formulation is optimized for follicular delivery with mechanical agitation for a certain period of time. After wiping off the formulation from the top of the skin, laser irradiation is performed, preferably with surface cooling. The laser is pulsed, with pulse duration approximately 0.5 ms-400 ms or, alternatively, from 0.5 ms-1,000 ms using a wavelength that is absorbed by the particle or the nanoshells. This method will permanently remove unpigmented or lightly pigmented hair by destroying the stem cells and other apparatus of hair growth which reside in the bulge and the bulb area of the follicle.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Topical Delivery of Nanoshells to the Follicular Epithelium for the Treatment of Follicular Diseases An example of massage as a mechanical means of follicular delivery is described. Nanoshell suspension tuned to 800-nm was massaged in an epilated pig skin in an in vivo live pig. Laser energy with parallel contact cooling was applied after wiping off the suspension on the top of the skin. A biopsy was taken, and routine histology was performed. A micrograph of the histology is shown at FIG. 1. Thermal damage to the follicular epithelium and part of the sebaceous gland is noted. Such damage is useful for the treatment of follicular diseases, such as acne or for improving the appearance of oily skin of a subject.

One exemplary method for the treatments above includes the step of topically applying a formulation comprising a sub-micron particle comprising a light absorbing materials to a subject's skin. Next, there is a step of facilitating delivery of said materials to a hair follicle, sebaceous gland, sebaceous gland duct, or infundibulum of the skin by mechanical agitation, acoustic vibration, ultrasound, alternating suction and pressure, or microjets. Thereafter, there is the step of exposing said sub-micron particle to energy activation, thereby treating the follicular skin disease.

Example 2

Topical Delivery of Nanoshells to the Follicular Epithelium for Laser Hair Removal In preparation for laser hair removal, a pig flank was epilated by waxing Skin was subsequently heated, and a vacuum was applied to empty the follicular contents of the skin. Silica core: gold shell microparticles, of approximate dimensions of 0.150 micrometers diameter coated with PEG were then delivered by massaging Skin was wiped to remove the material from the top of the skin. This was followed by pulsed laser irradiation at 800 nm. Samples were excised, fixed in formalin, and processed via routine histology (H&E staining). Thermal injury to the follicular structure was noted via histology.

Example 3

Light-Pulse Induced Pressure Pulse Facilitated Delivery

A formulation containing a light-absorbing material is applied on top of skin. This is moved into the infundibulum of the infundibulo-sebaceous unit by methods known in the art, including but not limited to, passive diffusion, heating, mechanical assistance such as pressure pulsing, vibration, acoustic coils, ultrasound, nozzles or a combination of the above. Then, pulses of light are applied with a handpiece with an integrated cooling plate that can be pressed on to the skin. The first pulse(s) of light heat the material, resulting in expansion, with or without steam bubble formation. A pressure pulse is thereby created. Pressure is applied to the skin by the plate during the pressure pulse. Because the pressure cannot escape from the skin, the material flows through low resistance channels within the skin, such as the sebaceous gland duct, to reach the sebaceous gland. This pulse typically has short pulse duration, e.g., 1 ns-1 ms, preferably, 10 ns-100 microseconds, to maximize the magnitude of the pressure pulse, for example, through steam bubble formation. Once the material is within the target sebaceous gland, light is applied with a pulse duration and radiant exposure appropriate to the size of the sebaceous glands being targeted. The light absorbing material is heated, causing thermal damage to the sebaceous gland, thus inactivating it, and causing improvement in acne vulgaris and other follicular diseases and conditions associated with the presence or activity of sebaceous glands.

In a related approach, a train of low-energy laser pulses, 1 microsecond or less in pulse duration, preferably in the acoustic range for pulse repetition rate, is used to activate the particles. This activation violently 'stirs' the particles, some of which will be propelled from the infundibulum into the sebaceous glands.

Example 4

Use of Ultrasound to Deliver Light Absorbing Material to the Follicle and Sebaceous Glands Pig ear skin was kept frozen. Before the experiment, it was thawed. Hair was epilated with waxing and a piece of the pig ear with skin facing up was placed at the bottom of a cup. It was filled with formulation of 150-nm diameter silica-core/gold-shell nanoshells (Sebacia, Inc., Duluth, Ga.) with an optical density of approximately 250. A Sonics, 20 kHz device horn was immersed into the formulation so that the distance between the far surface of the horn at the top of the skin was approximately 5-mm. The horn diameter was 13 mm and the power output was approximately 6 W. Thus, the power density during the on-time was 4.5 W/cm2. The device was turned on with 50% duty cycle, with the on-time and off-time per cycle of 5 s and 5 s, respectively. Four cycles were applied. After wiping the skin to remove excess formulation, the skin was irradiated with laser light at 800-m wavelength with a 9 mm.times.9 mm spot, approximately 50 J/cm2 total radiant exposure, and 30-ms pulse duration.

Figure 2:
FIG. 2 is a photograph showing the skin surface after application of the nanoshell formulation with ultrasound facilitated delivery. Excess formulation was wiped from the skin before this photograph was taken.
Figure 3:
FIG. 3 is a micrograph showing a follicle filled with dark colored nanoshells following ultrasound facilitated delivery. No nanoshells are noted in the epidermis or the dermis.
Figure 4:
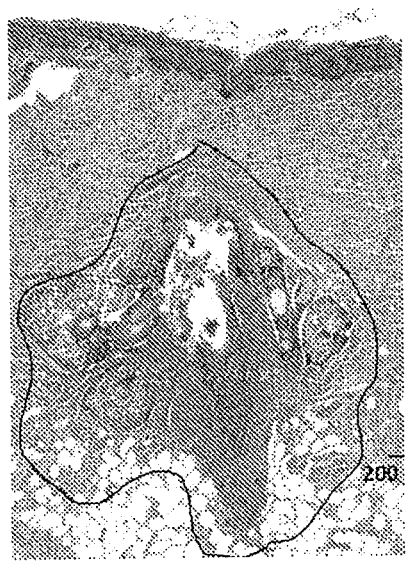
FIG. 4 is a micrograph showing a hair follicle and surrounding skin after ultrasound delivery of nanoshells and laser irradiation visualized by hematoxylin and eosin (H&E stain). Selective thermal damage around the follicle is shown by the added black delineation.

The skin was observed via a dissecting microscope and photographs were taken (FIG. 2). Cuts perpendicular to the skin surface were made through follicle openings and the cut surface was observed through an optical microscope (FIG. 3). Some samples were placed in 10% buffered formalin solution and observed via routine histology (FIG. 4).

The skin was intact and unperturbed except punctuate dots were noted on the follicle openings (FIG. 2). Upon cutting and observing through a microscope, the presence of dark nanoshells was noted within the follicle infundibulum, as well as in the sebaceous glands (FIG. 3). No nanoshells were seen in the epidermis or the dermis surrounding the follicles. Similarly, histology showed thermal damage to the follicular infundibulum and the sebaceous glands (FIG. 4). There was no or minimal damage to the epidermis and the dermis surrounding the follicles.

In one alternative aspect, in an method employing an ultrasound horn used for immersion ultrasound, the ultrasound horn face peak-to-peak amplitude displacement is in the range of 0.5 to 30 microns.

In still other aspects, there is provided a sub-micron particle size is selected for passage through the hair follicle and into a sebaceous gland of the hair follicle. In one embodiment, the hair follicle is a terminal follicle. In another embodiment, the hair follicle is a vellus follicle. In still another embodiment, the hair follicle is a sebaceous follicle. In still further implementations of the inventive methods described herein, the sub-micron particle size is between about 0.01 microns to about 1.0 microns. In still another exemplary implementation, the sub-micron particle size is between about 0.05 to about 0.25 microns.

Example 5

Ultrasound Facilitated Delivery

A transducer from APC International of Mackeyville, Pa. was driven by a sinusoidal wave of 300 Vp-p from a waveform generator and an amplifier with 500 Ohm source impedance. A formulation of 250 OD (F78, Sebacia, Inc.) containing the 150 nm diameter silica core: gold shell was placed topically on epilated pig ear skin. This was followed by wiping of the top surface and laser irradiation with Lumenis LIGHTSHEER at or about 800 nm. The skin temperature was noted after the ultrasound application and did not exceed 41. degree. C.

Figure 5:
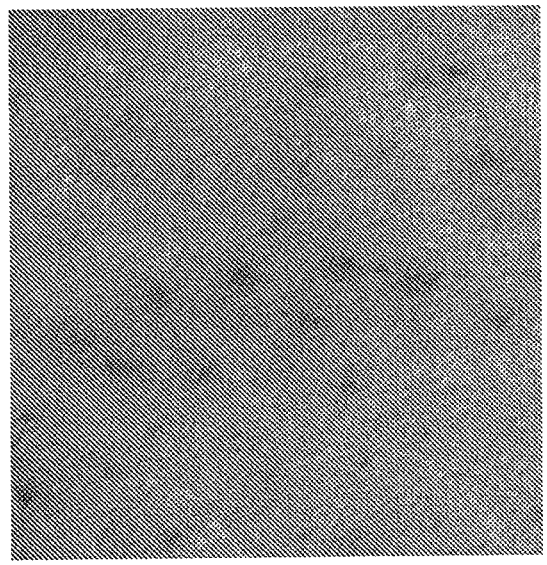
FIG. 5 is a photograph showing the skin surface. Accumulation of nanoshells in the follicles is seen.
Figure 6:
FIG. 6 is a micrograph showing a follicle having a significant accumulation of nanoshells.

Significant accumulation of the nanoshells in the follicles was noted (FIG. 5). Vertical cuts were made through follicles and the cut surfaces were observed under a microscope. An exemplary follicle is shown in FIG. 6. A significant accumulation of nanoshells inside and outside the infundibulum is noted.

Figures 7, 8:
FIG. 7 is a micrograph showing localized thermal damage to a follicle encompassing the sebaceous gland visualized using H&E stain.
FIG. 8 is a table showing the efficacy of nanoshell delivery followed by laser treatment in a human clinical trial of back acne.

Histological analysis of a sample is shown in FIG. 7. Localized thermal damage to the follicle including thermal damage to the sebaceous glands is observed (FIG. 7).

Example 6

Human Clinical Efficacy Demonstrated in Back Acne

The efficacy of nanoshell topical delivery followed by laser treatment was evaluated in a clinical study of back acne. Nanoshells were topically applied to the back of each subject and laser treatment was initiated as described herein above. This treatment regimen was administered twice to each subject. Results were evaluated twelve weeks following the second treatment. Efficacy was determined by weighted inflammatory lesion counts. Results are shown in FIG. 8. This study of back acne study indicates that the treatment regimen was clinically effective.

Example 7

Human Clinical Efficacy Demonstrated in Sebaceous Gland Damage

IRB approved human clinical studies have been carried out in seventeen subjects (6 males, 11 females) with acne. The subjects range in age from 18-40 years (mean 24 years) phototype I-IV. Treatment was carried out on a 1 square inch area behind ear (sebaceous follicles). Nanoshells were delivered followed by laser treatment, where the laser was tuned to the nanoshell's absorption peak (40-50 J/cm2, 30-ms, 9.times.9 mm, LIGHTSHEER (at or about 800 nm)). Therapeutic efficacy was histologically evaluated in 31 biopsies, where 4-7 follicles were present in each biopsy. A 4 mm punch biopsy was taken, serially sectioned, and damage to sebaceous follicle was visualized by H&E staining Pain, erythema, edema minimal. Localized damage was observed in .about.60% of sebaceous follicles. In some specimens, destruction of the entire sebaceous gland was observed. The depth of thermal damage in follicles was on average 0.47 mm (maximum 1.43 mm). No collateral damage to epidermis or dermis was observed. In-vivo histology study damage to infundibulum, bulge and sebaceous glands was observed after treatment.

Example 8

Ultrasound Facilitated Delivery of Photodynamic Therapy (PDT) with Aminolevulinic Acid (ALA)

In experiments with ultrasound, the follicle provided easier access for delivery of light absorbing materials than the stratum corneum. This may be due to a differential in the transport rates into the stratum corneum and the follicle. This difference can be exploited to facilitate selective delivery of smaller molecules. This approach can be used for either chromophores in a photothermal treatment regimen or for photodynamic therapy with compounds or prodrugs leading to photodynamic effect. For example, convention acne therapies involving ALA-PDT treatment require long incubation times (on the order of 3-4 hours) to deliver sufficient concentration of ALA to the sebaceous glands to achieve the desired clinical efficacy.

This treatment results in significant adverse side effects, including epidermal crusting, pain, and long-lasting redness. This extended incubation period results in the delivery of ALA to non-target areas of the epidermis and the dermis. Ultrasound-assisted delivery can be accomplished without these long incubation periods, while still achieving sufficient concentrations in the target infundibulo-sebaceous unit. Because the long incubation period is eliminated with ultrasound delivery, little ALA is delivered to the non-target epidermis and dermis. After ultrasound delivery, the ALA formulation can be removed from the skin surface. The light irradiation is performed once sufficient time has passed to ensure that concentrations of the photoactive material have reached adequate levels in the target volume. In photothermal treatments, pulsed laser irradiation can be initiated soon after delivery.

In another embodiment, materials (compounds) of interest are attached to microparticles and delivered to the target volume. Light irradiation may be used to disassociate the material, leading to its diffusion and subsequent action. Formation of cavitation bubbles is facilitated by the presence of nanoparticles that "seed" bubble formation. Also, delivery can be facilitated by the use of volatile components such as ethanol.

Example 9

Formulations

Various nanoshells formulation were tested in an ex vivo skin model. The components tested were designed to enhance delivery into follicles. Formulation constituents were ethanol, isopropyl alcohol, propylene glycols, surfactants such as polysorbate 80, Phospholipon 90, polyethylene glycol 400, isopropyl adipate. Compatibility of these amongst each other was tested. Three classes were identified: hydrophilic, lipophilic, and liposomal. The absorption coefficient of the formulation is suggested to be in the range of 10 to 1,000 inverse cm. Four example formulations were tested in an in vivo pig skin model; the compositions are as in Table 3 below showing four of the formulations tested in a human back acne study.

TABLE 3

| Components | F74 | F76 | F78 | F80 |
|---|---|---|---|---|
| PEGylated nanoshell suspension in water (Optical density ~1,100-1,200) | 12% | 25% | 25% | 65% |
| Ethyl Alcohol 190 proof | 73% | 55% | 54% | 20% |
| Propylene Glycol | 5% | 10% |  | 5% |
| Polysorbate 80 | 1% | 9% | 1% | 9% |
| Benzyl Alcohol | 9% | 1% |  | 1% |
| Diisopropyl Adipate |  |  | 20% |  |
| Total | 100% | 100% | 100% | 100% |

The desired effects from selective photothermolysis of sebaceous glands using any one or more of the above described delivery techniques, compositions or formulations can be enhanced by choosing an optimal treatment interval by retreating cells and tissue when they are most vulnerable to repeated thermal injury. The desired effects from selective photothermolysis of sebaceous glands using one or a combination of the above can be enhanced by choosing an optimal treatment interval. In one aspect, the treatment interval is selected by re-treating cells and tissue when they are most vulnerable to repeated thermal injury. In one aspect, the second or subsequent treatment occurs one, two, three, four, five or six days after the initial or just prior treatment. In one aspect, the interval between second and subsequent or the just prior treatment is the same or, optionally, different. In one aspect, the second or subsequent treatment occurs between 4-14 days after the previous treatment.

In one specific aspect, there is provided a mechanism of acne treatment through delivery of light absorbing particles into the sebaceous follicles selectively followed by pulsed laser irradiation that causes selective heating. Cell death occurs primarily due to heat fixation or protein denaturation though some occurs via apoptosis and accidental cell death. It is desired to achieve a high level of injury in one single treatment but without collateral damage and side effects. Due to various reasons including limited delivery of the particles possible in one treatment, the injury is limited and other factors a single treatment may not lead to complete resolution of acne. Second or additional subsequent treatments, given during the proper treatment interval, would likely enhance the clinical improvement and durability of the therapy.

Figure 9:
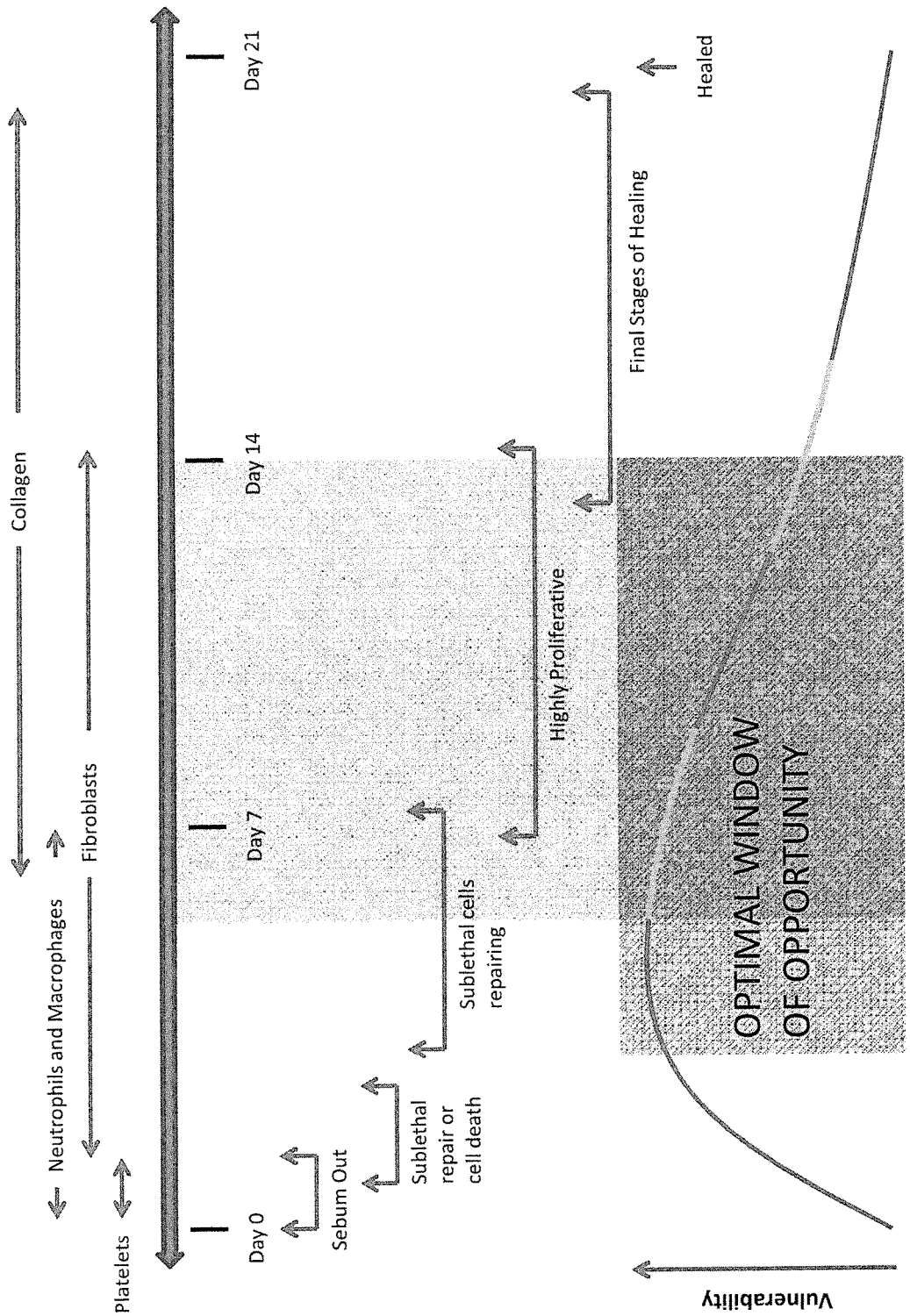
FIG. 9 illustrates in a general way the biologic response of cells and tissue to thermal injury as a function of time since thermal injury occurred.

FIG. 9 illustrates in a general way the biologic response of cells and tissue to thermal injury as a function of time since thermal injury occurred. Cells are most vulnerable to further damage after 4-14 days post-injury. Prior to day 4, body's response involves expression of various molecules including heat shock proteins which provide a cloak of protection. The heat shock protein peaks at 34 hours post treatment and is much reduced at 72 hours (See Laubach, et al., 2006, Skin Responses to Fractional Photothermolysis, Lasers in Surgery and Medicine Laubach Hans-Joachim, Tannous Zeina, Anderson R. Rox, Manstein Dieter, Lasers in Surgery and Medicine, Vol. 38, Issue 2, pages 142-149, February 2006, incorporated herein by reference.) Also, in the same work, Laubach showed that the cells showing loss of viability are almost undetectable at day 7. Thus at about day 7, two effects are noted: (1) the cloak of protection due to HSP is minimal and (2) the non-viable cells due to the treatment have almost disappeared.

These two effects in conjunction with other factors lead to various aspects of the present invention to provide for an optimal time-window to perform the next treatment, or a series of subsequent treatments, depending upon patient need or desired clinical outcome. FIG. 9 also shows that between 4-14 days, the cells with sub-lethal injury are repairing and there is proliferation of new cells due to the thermal injury. Both processes are active in this interval and hence, a new treatment would damage the cells in these two cycles. While desiring not to be bound by theory, it is believed that a treatment timed to this interval would enhance the treatment effect.

It is also possible that the window for the next treatment starts at 24 hours—a higher energy could do permanent damage to the already damaged tissue including cells. Also, the sebum is expelled at around 24 hours and the infundibulum would be most clear at that time. This would allow for the most efficient delivery during the next treatment. Also, there may be residual particles present from the previous treatment and a treatment at 24 hours would target the previously delivered particles as well as the newly delivered with the high efficiency afforded by the empty infundibulum.

This first set of treatments will typically consist of 1-5 treatments. This is expected to give a treatment response of 8-12 months. After this period, further treatment is necessary to obtain remission in acne symptoms. This can be obtained by giving another set of treatments, again with a similar interval of 4-14 days.

Figure 10:
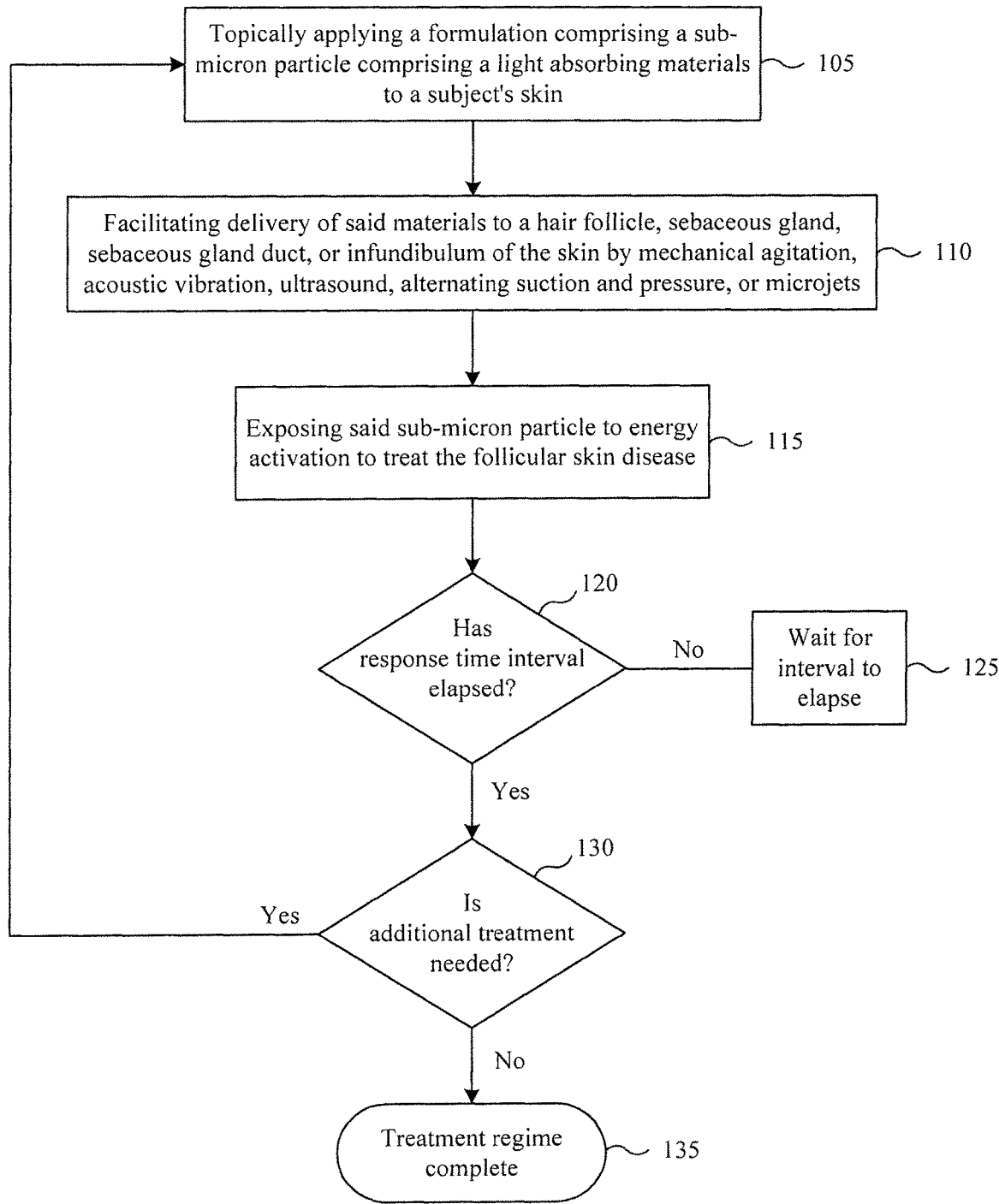
FIG. 10 is a flow chart of an exemplary method of providing therapy based on a desired response interval.

FIG. 10 is a flow chart of an exemplary method 100 of providing therapy based on a desired response interval. First at step 105, is the topical application of a formulation to the skin of the patient at the treatment site. Next, at step 110, there is the step of facilitating the delivery of the materials into the skin of the treatment site. Thereafter, is the exposure of the particles in the treatment site to an appropriate energy activation source (step 115). After this initial treatment (step 115), the user then waits for the desired response interval to elapse. The response interval may be measured in a variety of ways. In one aspect, the treatment interval is based on time (as in the days indicated on FIG. 9). In one aspect, the treatment interval is based on the state of initial, partial or complete repair of specific tissue or combinations of tissue (as detailed in FIG. 9). In still another aspect, the treatment interval is based on the state of the initial, partial or complete biologic response of specific tissue or combinations of tissue (as detailed in FIG. 9).

If the answer to step 120 is "NO" then the user waits until the response time has elapsed (step 125).

If the answer to step 120 is "YES" then the user determines whether the treatment plan or clinical situation calls for an additional treatment. If an additional treatment is to be delivered, (Answer to step 130 is "YES") then the user proceeds to perform steps 105, 110 and 115 as desired based on any of the above described techniques. The second or subsequent formulation, method or methods of facilitating delivery as well as type and exposure of energy activation may be the same or different from the initial or just previous performance of the method.

If the answer to step 130 is "NO" then the user determines whether the treatment plan or clinical situation does not call for an additional treatment. The treatment is concluded (step 135).

Other Embodiments

The examples and illustrations included herein show, by way of illustration and not of limitation, specific embodiments in which the subject matter may be practiced. In one aspect, the operation of the delivery device for the delivery of a delivery fluid is the desired therapy. In this case, the operation of the delivery device is a complete treatment operation. In another aspect, the operation of the delivery device for the delivery of a delivery fluid precedes or follows another treatment or another desired therapy. In this case, the operation and use of the delivery device is one part of a multi-part therapy. In one specific example of a multiple part therapy is the use of the delivery system to deliver a fluid, a formulation particles, shells, pharmaceuticals, liposomes, other treatment agents or pharmacologic materials onto, into or within a structure within a treatment or delivery site followed by a further treatment of the delivery or treatment site. In one specific example the further treatment is providing an activating energy to a fluid, a formulation or a pharmacologic material. Exemplary fluids, formulations and treatments are described in U.S. Pat. Nos. 6,183,773; 6,530,944; U.S. Patent Application Publication No. US 2013/0315999 and U.S. Patent Application Publication No. US 2012/0059307, each of which is incorporated herein in its entirety. Additionally or optionally, one or more of the delivery device operating parameters, and/or methods of use of the delivery system described herein may be modified based upon one or more characteristics of the delivery fluid, a component of the delivery fluid or a particle within the delivery fluid being used.

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

What is claimed is:

1. A method of at least one of treating and ameliorating acne vulgaris in a subject, the method comprising:
   a. a first phase of treatment, said first phase of treatment comprising:
      i. topically applying a first formulation comprising plasmonic nanoparticles in a hydrophilic solution to a subject's skin of a face or an upper trunk, said first formulation having an optical density of between about 5 and about 500;
      ii. mechanically agitating said first formulation on said skin to facilitate delivery of said nanoparticles to at least one of the group of a hair follicle, a sebaceous gland, a sebaceous gland duet, and an infundibulum of the skin; and iii. irradiating said nanoparticles with light having a wavelength between about 700 and about 1,100 nm that is absorbed by said nanoparticles, thereby heating said skin local to said nanoparticles for at least one of treating and ameliorating acne vulgaris; and
b. a second phase of treatment, said second phase of treatment comprising:
   i. between about 23 hours and 14 days after said irradiating step of said first phase of treatment:
      a. topically applying a second formulation comprising said nanoparticles to said subject's skin, said second formulation having an optical density of between about 5 and about 500;
      b. mechanically agitating said second formulation on said skin to facilitate delivery of said nanoparticles to at least one of the group of a hair follicle, a sebaceous gland, a sebaceous gland duct, and an infundibulum of the skin; and
      c. irradiating said nanoparticles with light having a wavelength between about 700 and about 1,100 nm that is absorbed by said nanoparticles, thereby heating said skin local to said nanoparticles for at least one of treating and ameliorating acne vulgaris.

2. The method of claim 1 further comprising a third phase of treatment after said second phase of treatment comprising, between about 23 hours and 14 days after said second phase of treatment, repeating the topically applying, mechanically agitating and irradiating steps of the second phase of treatment.

3. The method of claim 2 further comprising a fourth phase of treatment comprising, between about 8 and 12 months after said third phase of treatment, repeating the topically applying, mechanically agitating and irradiating steps of the second phase of treatment.

4. The method of claim 3 further comprising a fifth phase of treatment, between about 23 hours and 14 days after said fourth phase of treatment, repeating the topically applying, mechanically agitating and irradiating steps of the second phase of treatment.

5. The method of claim 4 further comprising a sixth phase of treatment, between about 23 hours and 14 days after said fifth phase of treatment of claim 4, repeating the topically applying, mechanically agitating and irradiating steps of the second phase of treatment.

6. The method of claim 2 wherein the third phase of said topically applying, mechanically agitating and irradiating steps is performed about 4 days after said second phase of treatment.

7. The method of claim 2 wherein the third phase of said topically applying, mechanically agitating and irradiating steps is performed about 5 days after said second phase of treatment.

8. The method of claim 2 wherein the third phase of said topically applying mechanically agitating and irradiating steps is performed about 6 days after said second phase of treatment.

9. The method of claim 1 further comprising, between about 23 hours and 14 days after said second phase of treatment, making a clinical evaluation of whether said subject needs further at least one of treating and ameliorating acne vulgaris, and if said subject needs further treatment repeating the topically applying, mechanically agitating and irradiating steps before 14 days have lapsed since said second irradiating step of the second phase of treatment.

10. The method of claim 1 wherein the nanoparticles are within a sebaceous gland during the irradiating steps.

11. The method of claim 1 wherein the nanoparticles are within an infundibulum involved in the acne vulgaris.

12. The method of claim 1 wherein the nanoparticles have a size that is between about 0.05 to about 0.25 microns.

13. The method of claim 1 wherein the nanoparticles are coated with PEG.

14. The method of claim 1 wherein the nanoparticles are nanoshells.

15. The method of claim 1 wherein energy activation of the nanoparticles is accomplished with a pulsed laser light that delivers light energy at a wavelength that is absorbed by the nanoparticles.

16. The method of claim 1 wherein the first and second formulations comprise the same formulation.

17. The method of claim 1 wherein the nanoparticles comprise at least one of gold and silver.

18. The method of claim 1 wherein the nanoparticles are gold nanoshells with a peak absorption between 700 and 1,100 nm wavelength of light.

19. A method of at least one of treating and ameliorating acne vulgaris in a subject, the method comprising:
   a. topically applying a first application of a formulation comprising one or more plasmonic nanoparticles in a hydrophilic solution comprising at least one of the group consisting of gold, silver, and combinations thereof to a skin structure of a face or an upper trunk with acne vulgaris;
   b. facilitating delivery of said nanoparticles to said skin structure by mechanical agitation;
   c. irradiating said nanoparticles with light having a wavelength that is absorbed by said nanoparticles, thereby heating the localized environment of said nanoparticles for at least one of treating and ameliorating said acne vulgaris; and
   d. between about 4 and 6 days after said irradiating step, repeating said topically applying, facilitating and irradiating steps to the skin structure for a second application.

20. The method of claim 19 in which said skin structure comprises at least one member of the group consisting of a hair follicle, a sebaceous gland, a sebaceous gland duct, and an infundibulum.

21. The method of claim 20 further comprising a third application of said topically applying, facilitating and irradiating steps that is performed between about 4 and 6 days after said second irradiating step.

22. The method of claim 21 further comprising after the third application, repeating said topically applying, facilitating and irradiating steps, between about 4 and 6 days after said third irradiating step, for a fourth time.

23. The method of claim 21 further comprising repeating said topically applying, facilitating and irradiating steps between about 8 and 12 months after said third application of said topically applying, facilitating and irradiating steps.

24. The method of claim 23 further comprising repeating said topically applying, facilitating and irradiating steps, between about 4 and 6 days after said third application of said topically applying, facilitating and irradiating steps.

25. The method of claim 21 wherein the time between the second and third applications of said topically applying, facilitating and irradiating steps is about 4 days.

26. The method of claim 21 wherein the time between the second and third applications of said topically applying, facilitating and irradiating steps is about 5 days.

27. The method of claim 21 wherein the time between the second and third applications of said topically applying, facilitating and irradiating steps is about 6 days.

28. The method of claim 19 wherein said nanoparticles are within a sebaceous gland during irradiation.
29. The method of claim 19 wherein said nanoparticles are within an infundibulum involved in the acne vulgaris.
30. The method of claim 19 wherein said nanoparticles are coated with PEG.
31. The method of claim 19 wherein said nanoparticles are nanoshells.
32. The method of claim 19 wherein said nanoparticles have a diameter of about 50 to about 250 nm.
33. The method of claim 19 wherein the irradiating step uses light energy at a wavelength range from about 700 to about 1,100 nm.
34. The method of claim 19 wherein the irradiating is achieved using a light energy that has a fluence of less than about 100 J/cm2.
35. The method of claim 19 wherein said skin structure is prepared for the method by selecting at least one member of the group consisting of by heating, by removing the follicular contents, by epilation, and by contacting the follicle pore with adhesive polymers.
36. The method of claim 19 wherein the formulation has an optical density of between 5-500.
37. The method of claim 19 wherein the nanoparticles are gold nanoshells.
38. A method for at least one of treating or ameliorating acne vulgaris in a subject, the method comprising:
  a. a first phase of treatment, said first phase of treatment comprising:
    i. topically applying a formulation comprising nanoparticles in a hydrophilic solution comprising a light absorbing material to a subject's skin of a face or an upper trunk:
    ii. facilitating delivery of said nanoparticles to at least one of the group of a hair follicle, a sebaceous gland, a sebaceous gland duct, and an infundibulum of the skin by mechanical agitation; and
    iii. irradiating said nanoparticles with light having a wavelength that is absorbed by said nanoparticles, thereby heating the localized environment of said nanoparticles for at least one of treating and ameliorating acne vulgaris
  b. a second phase of treatment, said second phase of treatment comprising, between about 4 and 6 days after said irradiating step of said first phase of treatment:
    i. topically applying a formulation comprising said nanoparticles comprising said light absorbing material to the subject's skin:
    ii. facilitating delivery of said nanoparticles to at least one member of the group consisting of a hair follicle, a sebaceous gland, a sebaceous gland duct, and an infundibulum of the skin by mechanical agitation; and
    iii. irradiating said nanoparticles with light having a wavelength that is absorbed by said nanoparticles, thereby heating the localized environment of said nanoparticles for at least one of treating and ameliorating acne vulgaris.
39. The method of claim 38 further comprising, between about 4 and 6 days after said second phase of treatment, repeating the topically applying, facilitating and irradiating steps of the second phase of treatment for a third phase of treatment.
40. The method of claim 39 further comprising, between about 4 days and 6 days after said third phase of treatment, repeating the topically applying, facilitating and irradiating steps of the second phase of treatment for a fourth phase of treatment.

* * * * *